United States Patent [19]

Thomas et al.

[11] 4,009,257

[45] Feb. 22, 1977

[54] PREPARATION OF IMMUNOSUPPRESSIVE MATERIALS

[75] Inventors: Derek Thomas, West Wickham; Heddy Zola, Rugby, both of England

[73] Assignee: Burroughs Wellcome, Inc., Research Triangle Park, N.C.

[22] Filed: Feb. 24, 1971

[21] Appl. No.: 118,532

[30] Foreign Application Priority Data

Feb. 27, 1970 United Kingdom ............... 9647/70

[52] U.S. Cl. .................................. 424/85; 424/101
[51] Int. Cl.$^2$ .................. A61K 35/14; A61K 35/26
[58] Field of Search ...................................... 424/85

[56] References Cited

OTHER PUBLICATIONS

Culliton, Science News, vol. 95, pp. 457–459, May 1969.
Korngold et al., J. Nat. Cancer Inst., vol. 26, pp. 547–565, 1961.
Antilymphocytic Serum, Ciba Foundation Study Group No. 29, published by J. & A. Churchill Ltd., London, 1967, pp. 102–107, 128, 129, 142, 143, 150, & 151.
Chemical Abstracts (1), vol. 62, entry 5727f, 1965.
Chemical Abstracts (2), vol. 70, entry 93123a, 1969.
Chemical Abstracts (3), vol. 72, entry 1961z, 1970 citing James et al.
Immunochemistry, vol. 6, No. 5, pp. 659–680, 1969.
Naharian et al., Annals of Surgery, vol. 170, No. 4, pp. 617–632, Oct. 1969.

*Primary Examiner*—Shep K. Rose
*Attorney, Agent, or Firm*—DeLio & Montgomery

[57] ABSTRACT

A soluble immunogenic extract of human blood lymphocytes, a non-toxic immunosuppressive antilymphocytic serum raised by the extract, a non-toxic immunosuppressive antilymphocytic immunoglobulin G derived from the serum, and methods of isolating the extract, raising the antiserum and isolating the immunoglobulin G.

11 Claims, No Drawings

PREPARATION OF IMMUNOSUPPRESSIVE MATERIALS

The present invention relates to lumphocyte extracts, and in particular to lymphocyte extracts which are suitable for the production of non-toxic immunosuppressive antisera, from which can be isolated non-toxic immunosuppressive antilymphocytic immunoglobulin G (A.L.G.)

The properties of immunosuppressive antisera, especially antilymphocyte sera (A.L.S.), have been studied for some time in connection with the problem of homograft rejection in transplant surgery. This rejection is due to the immunological incompatability between the recipient and the donor of the homograft, and attempts to combat this have involved tissue matching and the administration of certain immunosuppressive drugs.

A.L.S., which is produced in mammals in response to the parenteral introduction of lymphocytes or lymphocyte antigens, has been found to suppress the rejection of homografts in mammals. A.L.S. from a number of sources has been tested in various animals, and one problem that has arisen is that particular A.L.S.'s have some undesirable and often toxic activities, such as antibody activities against red blood cells and platelets, in addition to their immunosuppressive action.

These adverse side-effects have seemed to be tissue related. Rodent and human thymocytes (that is, lymphocytes from the thymus), subcellular fragments and especially the cell membranes of such thymocytes, and soluble extracts of such thymocytes and in particular the specific extract known as thymosin have been used to produce immunosuppressive antisera which are non-toxic. Similarly, calf thymosin has been so used.

The quantities of lymphocytes available from thymi are not, however, sufficient for economic commercial production of immunosuppressive antisera. The most readily available human lymphocytes are from human blood, but the immunosuppressive antisera raised against such cells and even the membranes of such cells are toxic, and in particular cause a substantial reduction in the number of red blood cells and platelets of the animal to which they are administered, for example, by agglutination, lysis and other mechanisms.

It has now been found that soluble extracts of human blood lymphocytes can be used as a source of immunogen for raising an immunosuppressive A.L.S. from which can be isolated an immunosuppressive A.L.G., both of which are devoid of the toxic properties normally characteristic of the A.L.S. raised to particulate extracts of human blood lymphocytes or to the whole cells.

According to the present invention there is therefore provided a sterile preparation suitable for raising non-toxic and immunosuppressive antilymphocytic antiserum in a mammal other than man comprising a soluble immunogenic extract of human blood lymphocytes said extract being isotonic with the blood of the mammal to be used.

A particularly valuable form of this preparation is a sterile, soluble immunogenic extract of human blood lymphocytes which comprises primarily a mixture of macromolecular components each of which has a molecular weight less than 1,000,000 and greater than 10,000, the mixture having a protein content of between 50% and 100%, a lipid content below 30% and preferably below 10%, and a carbohydrate content below 20%, the percentages being by weight of dry weight of the extract excluding salts. In this context, the term 'salts' means component substances of the extract, each of which has a molecular weight less than 5,000.

The molecular weight and percentage composition values quoted above are subject to variation within the limits set forth due to such factors as the state of health and age of the human, or the conditions of a cell culture, from which the blood lymphocytes are obtained. Advantageously, the molecular weight of the macromolecular components lies between 10,000 and 200,000, preferably below 100,000, for example, about 60,000.

As used herein with reference to A.L.S. or A.L.G., the term "immunosuppressive" means having the ability to reduce the intensity of an organism's reaction against incompatible tissue, that is foreign tissue or the organism's own tissue when this becomes incompatible; thus the term "immunosuppression"is intended to include specifically the prolongation of the life of grafts, especially homografts, following transplant surgery, and also the treatment of auto-immune disease such as sympathetic opthalmia.

As used herein with reference to A.L.S. or A.L.G., the term "non-toxic" means that the A.L.S. or A.L.G. produces little or no agglutination when mixed with human red blood cells, and no bleeding and little or no fall in blood platelet count in mice at 18 hours after injection intraperitoneally of 1 ml. of the A.L.S. or A.L.G.

The antigenic extract is "soluble" in the sense that 10 mg. in 1 ml. of 0.85% w/v aqueous sodium chloride solution is visually a clear solution. Most preferably the extract contains no particles greater in size than $0.22\mu$; this may be readily achieved by centrifugation at 100,000 g for 30 minutes, and by passage through a Millipore (Registered Trade Mark) GS filter with a pore size of $0.22\mu$, although it should be noted that generally centrifugation, under the conditions specified above, is sufficient in itself in effecting removal of any particles greater in size than $0.22\mu$.

According to the present invention there is also provided a method for preparing a soluble, sterile, immunogenic extract of human blood lymphocytes as hereinbefore defined comprising lysing the lymphocytes and isolating the soluble extract from the lysate, and rendering the extract sterile and isotonic with the blood of the mammal to be used.

A suitable source of human blood lymphocytes may be a collection of cultured lymphocytes originally obtained from fresh blood, and then cultured on an appropriate nutrient medium until required. A particularly advantageous feature of the present invention, however, is that the blood lymphocytes to be used may be readily isolated from human fresh blood, a fairly easily obtainable source. This may be done in any known manner, but conveniently the blood is citrated, recalcified and defibrinated before sedimentation of the erythrocytes. The lymphocytes are then separated from the supernatant, and any residual red blood cells are removed.

Lysis of the lymphocytes may be carried out by any conventional technique for cell lysis, including mechanical lysis, for example by use of ultrasonic sound waves or intracellular cavitation to achieve rupture of the cells. It is preferred, however, to lyse the lymphocytes by the use of physicochemically acting agents, for example, hypertonic buffers, and then mechanically agitate the viscous lysate to disperse it before isolating the extract; or by the use of physiocochemically acting agents, for example, hypotonic buffers, in conjunction with mechanical agitation aiding the lysis.

Thus from the viewpoint of manufacturing convenience, batch quantity and quality of the product, it is peferred to lyse with hypertonic or hypotonic aqueous buffer solutions. More specifically, hypotonic or hypertonic lysis comprises the suspension of the lymphocytes in an aqueous hypotonic or hypertonic buffer respectively and shearing the cell debris with a suitable homogeniser, for example a Dounce homogeniser (Jencons Ltd., London) using 50 to 100 reciprocal strokes of the piston. Occasionally the Dounce homogeniser may prove ineffective in producing satisfactory disintegration of the cell debris in which case another homogeniser may be tried. In such instances, it has been found that the Silverson homogeniser (Silverson Machines Ltd., London) is generally satisfactory if use for about two minutes at medium speed.

Any buffer known in the art as a suitable medium for hypotonic or hypertonic lysis may be used, but the pH of any buffer used is preferably about 7.5. Particularly suitable buffers are those set forth in the Examples set forth below.

Lysis using the ultrasonic technique may be achieved in the manner described in the literature (Ref. 8). This essentially involves subjecting a suspension of the lymphocytes in an aqueous buffer to ultrasonic waves in an ultrasonic oscillator for a period of time varying from 1 to 30 minutes. Likewise, lysis using intracellular cavitation may be carried out in a known manner, for example, by subjecting a suspension of the lymphocytes in an aqueous buffer of a pH of about 7.6, to a high pressure of nitrogen, for example between 500 and 1000lb/sq.in., but preferably at 800lb/sq.in., in a steel pressure vessel, also known as a nitrogen bomb, followed by release of the pressure so causing rupture of the lymphocytes.

The lymphocytes may also be lysed by subjecting them to an aqueous solution of an ammonium or alkali metal thiocyanate salt, preferably a 1.3 to 3M solution of potassium thiocyanate, though the sodium salt is also of particular value. Cell lysis is achieved immediately giving a very viscous suspension which may then be diluted with an aqueous sodium chloride solution and dispersed using an homogeniser.

Throughout the procedures involved in lysing the lymphocytes and subsequent stages in isolating the extract, a low temperature is maintained in order to avoid side reactions and consequent loss of material, for example by enzymic degradation. A temperature between 0° and 10° C, preferably about 4° C, has been found convenient.

Following lysis of the human lymphocytes, it is necessary to isolate the soluble extract. This involves separating the soluble material from the insoluble matter in the lysate and where a thiocyanate salt has been used in the lysis, then the step of isolation additionally includes the removal of the thiocyanate ion by any standard procedure, and references to 'isolation' of or 'isolating' the extract are to be understood to have this meaning. Prior to use of the extract for raising an A.L.S. in a mammal other than man, it is also necessary to ensure that the extract is isotonic with the blood of that mammal, and that the extract is sterile. The latter may be achieved either as a separate step of sterilization, or by virture of one or more of the steps involved in the isolation procedure itself.

Isolation of the soluble fraction of the lysate may be performed by any method known in the art for separation of soluble cell material from insoluble cell debris, but preferably by ultracentrifugation with or without a subsequent membrane filtration of the soluble fraction. Ultracentrifugation may be advantageously carried out at 60,000 to 150,000g, for 20 to 50 minutes. In this way the soluble material of the lysate is separated from the particulate matter mainly made up of membranes, nuclei and other subcellular particles.

If ultracentrifugation does not achieve the desired separation of the soluble and insoluble material of the lysate, then a further separation can be carried out by means of membrane filtration, for example using a Millipore (Trade Mark) GS membrane with a pore size of $0.22\mu$. This procedure removes any residual particulate components and is also effective in sterilizing the extract.

If a thiocyanate salt has been used in the lysis of the cells, then the thiocyanate ion may be conveniently removed by dialysis. If a hypertonic buffer has been used in the lysis of the cells, then the salts which constitute the hypertonic buffer may be conveniently removed by dialysis. It is also helpful, though not necessary, to dialyse the soluble fraction when obtained by hypotonic lysis to adjust the salt content of the soluble fraction. Dialysis also has the additional advantage of removing low molecular weight components which do not appear to contribute to the immunogenicity of the final extract. Dialysis is generally carried out against an aqueous solution of 0.85% w/v sodium chloride.

As an additional and optional step, the soluble fraction may also be concentrated by any known means, but advantageously by ultrafiltration. In this step, removal of the low molecular weight proteins can also be achieved depending upon the pore size of the membrane used, the said pore size in any event not exceeding a value such that molecules of molecular weight greater than 10,000 are excluded.

The step of membrane filtration referred to above may be carried out before dialysis or concentration, if the latter steps are employed and after centrifugation, but advantageously after these steps if they produce traces of insoluble matter, and after storage of the extract, if needed.

The chemical nature of the soluble extract may be ascertained by any convenient method. The protein content may be estimated from the ratio of the optical density at $260\ \mu$ to the optical density of $280\ \mu$ (Ref. 3), the optical densities being determined by scanning suitable dilutions in a Unicam (Registered Trade Mark) S.P. 800 spectrophotometer. It is peferably determined using the Lowry method (Ref. 4) based on the intensity of the blue colouration obtained by the reaction of the protein with the reagent used in the Lowery Method. The lipid content may be estimated from the chloroform solubility of an acid hydrolysate of the extract (Ref. 5). The acid hydrolysis may conveniently be affected by hydrochloric acid. The carbohydrate content may be determined by the anthrone method (Ref. 6) based on the intensity of the colour developed in the reaction of the carbohydrate with anthrone.

The molecular weight of macromolecular components of the extract, as quoted above, were determind by ultracentrifugation studies for determining the sedimentation coefficient and deriving an empirical molecular weight from this using the equation of Halsall (Ref. 1).

In another aspect of this invention there is provided an immunosuppressive sterile, isotonic and non-tonic A.L.S. raised against a soluble immunogenic extract of human blood lymphocytes as hereinbefore described in a mannal other than man. Thus the soluble extracts may be used to produce an A.L.S. by injecting them into mammals, other an man, conveniently using a mammal of the Orders Perissodactyla or Artiodactyla, for example, sheep, goats, cattle, pigs, or horses, by any convenient immunization schedule. In particular they may be used to immunize rabbits or horses according to the Lance schedule, (Ref. 7)which consists essentially of one intramuscular injection of the extract in Freund's Complete Adjuvant, that is, a water-in-oil emulsion of the dispersed liquid extract phase in a mineral oil, for example paraffin oil, also containing heat killed bacteria, followed by a course of four intravenous injections, spread over 6 weeks. Antibiotics, particularly streptomycin and polymyxin, may be added to the antigen to reduce adverse side-effects.

The A.L.S. raised in the immunized mammal is obtained by removal of the blood and subjecting it to clotting. Following removal of the clot, the antiserum may be inactivated, for example by heating at 50° to 65° C, in order to inactivate any enzymes which may be capable of degrading the A.L.S., and any complement which may interfere with the use of and tests for the A.L.G. fraction.

The A.L.S. may subsequently be fractionated to yield A.L.G., which comprises most of the immunoglobulin G. of the A.L.S. by using known techniques for the fractionation of sera.

The fractionation may be achieved by any method known in the art for obtaining immunoglobulin from antisera. Numerous methods used are applicable to obtaining immunoglobulin G from A.L.S. of the present invention.

In general, the process of fractionation involves separation of the globulins from the albumins of the A.L.S., removal of the haemolysins and haemaglutinins if present, and isolation of the immunoglobulin G though fractionation may also be achieved by immunoabsorption techniques whereby, for example, an antibody/antigen complex is formed and subsequently dissociated, to yield the desired antibody, in the form of immunoglobulin G. Alternatively, the immunoglobulin G may be obtained directly from the blood source using a plasmaphoretic technique. Separation of the globulins is conveniently effected by salt fractionation, preferably using ammonium or sodium sulphate. The haemolysins and haemaglutinins may be removed by absorption by red cell stroma, batchwise or in a column of agar gel grains containing the stroma. Immunoglobulin G may be isolated from the globulins, or directly frm the A.L.S. by one or more of several known techniques, which include electrophoretic techniques such as electrodecantation; zonal centrifugation; ion exchange chromatography, batchwise or in a column using, for example, a polysaccharide based anion exchanger such as DEAE cellulose or DEAE Sephadex (Trade Name, Pharmacia Ltd., Uppsala, Sweden); exclusion chromatography, batchwise or in a column; partition chromatography using inorganic gells such as calcium phosphate; or selective precipitation of protein with n-octanoic acid (Ref. 15).

The usual form of presentation as a pharmaceutical composition for therapeutic purposes of A.L.S. or A.L.G. is as a sterile isotonic aqueous solution of normally 5 to 10% w/v protein and 0.85% w/v sodium chloride, a stabiliser such as glycine preferably being included. Another form of presentation is as a freeze-dried powder having the same additives, for reconstitution with sterile water immediately prior to use. Administration is generally by intramuscular injection, or most preferably by intravenous infusion after any necessary dilution with isotonic saline solution. The dose range is normally 3 to 20 mg. of protein per kg. body weight per day. Thus, it is usual to administer from about 1 ml. per day of the sterile solution defined above for a child; and up to 15 ml. per day of the solution for an adult, subject to the discretion of the attending physician.

The present invention therefore provides a sterile and isotonic preparation of a non-toxic and immunosuppressive antilymphocytic immunoglobulin G derived by fractionation of an immunosuppressive and non-toxic antilymphocytic serum raised against a soluble immunogenic extract of human blood lymphocytes in a mammal other than man; and the methods hereinbefore described for preparing the said immunoglobulin G and antiserum.

The present invention also provides, in other aspects, the antilymphocytic serum and immunoglobulin G, whenever prepared by the techniques herein described.

In order that the invention may be more fully understood, the following examples are given purely by way of illustration and should not be regarded as limiting the scope of this invention.

EXAMPLE 1:

Preparation of a soluble antigenic extract of human blood lymphocytes by hopotonic lysis.

Fresh human blood was centrifuged at 1000 g for 30 minutes to obtain "buffy coat", which comprises a layer of white cells and platelets on the surface of red cells. The "buffy coat" was mixed with sodium citrate to prevent clotting. When required, 200 ml. of it were recalcified by the addition of calcium chloride so as to enable clotting to occur. The fibrin clot was removed mechanically, and the cell suspension was treated with a mixture of 50 ml. of 6% w/v dextran (molecular weight 110,000), 10 ml. of 10% w/v ethylenediaminetetraacetic acid, and 0.238 g. heparin, for one hour at room temperature. The erythrocytes were sedimented by this treatment, and the leucocyte-rich supernatant was passed through a column of polystyrene beads to isolate the lymphocytes. The residual red blood cells were removed by the addition of sufficient chicken anti-human erythrocyte serum to achieve agglutination, followed by centrifugation at low speed. 97% of the resulting cells were small lymphocytes, with a high (98%) viability, as shown by the exclusion of trypan blue, indicating the cell membranes were still semipermeable (Ref. 10). The lymphocyte preparation was examined microscopically and found to be uncontaminated by platelets or red blood cells.

A suspension of the cells, containing $5 \times 10^9$ lymphocytes, was centrifuged at 500 g for 10 minutes, and the resulting pellet was resuspended in 20 ml. of a cold (about 4° C) aqueous hypotonic buffer pH 7.4 sodium chloride, 0.01 M. containing 0.01 M.[2-amino-2-(hydroxymethyl)-propane-1,3-diol, and 1.5 mM magnesium chloride. The suspension was allowed to stand at 4° C for 30 minutes, and was then transferred to a tight-fitting glass piston/cylinder (Dounce) homogeniser kept in an ice-water bath. The cells were subjected to shearing in the homogeniser until at least 80% lysis was achieved, the degree of lysis being ascertained by intermittent sampling and microscopic examination. The cell lysate was centrifuged at 100,000 g for 30 minutes, and the clear supernatant was collected.

It had the following characteristics:

i. Solubility: it was a clear solution when examined visually; it remained clear when concentrated, up to 10 mg. of protein per ml., by ultrafiltration, following reconstitution after freeze-drying, and when the sodium chloride concentration was increased up to 0.85% w/v; and it passed through a Millipore GS filter indicating the absence of particles having a size greater than $0.22\mu$.

ii. Protein content: about 52% of dry weight of solid including salts, as previously defined. This was estimated by the method of Lowry (Ref. 4) in which the intensity of the blue colour produced, was measured in a spectrophotometer at 750 m$\mu$.

iii. Lipid content: about 7.4% of dry weight of solid including salts, as previously defined. This was estimated from the chloroform solubility (Ref. 5). A sample of the extract was hydrolysed in N-hydrochloric acid for 2 hours at 100° C, the hydrolysate was lyophilised, and the residue extracted with a mixture of chloroform and methanol in the ratio of 3 to 1 by volume; the solution was then extracted with 1 volume of water, the chloroform phase was lyophilised and the residue weighed.

iv. Carbohydrate content: about 1.3% of dry weight of solid including salts, as previously defined. The total carbohydrate content was measured by the anthrone method (Ref. 6); a sample was treated with 85% sulphuric acid at 100° C for 10 minutes in the presence of anthrone, and the intensity of the colour developed was measured in a spectrophotometer at 620 m$\mu$.

v. Molecular weight: the mixture of components had a molecular weight, as determined by ultracentrifuge studies (Ref. 1), principally around 100,000, though there was some material of higher molecular weight ranging up to but not above 1,000,000.

vi. Acrylamide gel electrophoresis: the extract was shown to be a mixture of many proteins. It separated into about twenty bands, although none indicated a major constituent. These results were obtained by the methods of Davis et al (Ref. 2).

EXAMPLE 2:

Preparation of a soluble antigenic extract of human blood lymphocytes by chemical extraction.

Lymphocytes were isolated from fresh human blood by the method described in Example 1.

The suspension of the lymphocytes thus obtained was cooled to 4° C, and treated with 1 volume of cold, aqueous 2 M potassium thiocyanate solution. A gel formed immediately, and this was allowed to stand at 4° C for 1 hour. The gel was then dispersed in 4 volumes of phosphate buffered normal saline, using a Silverson (Trade Mark, Silverson Machines Ltd., London) homogeniser, and the suspension was centrifuged at 100,000 g. for 30 minutes. The thiocyanate ion was removed by dialysis of the supernatant against phosphate buffered saline, and any formed precipitate was discarded. Finally, the solution was filtered through a Millipore GS filter with a pore size of $0.22\mu$, and the filtrate was collected.

The filtrate had substantially the same properties as the extract of Example 1, except that it appeared to have a higher protein content.

EXAMPLE 3

Preparation of non-toxic immunosuppressive anti-human immunoglobulin G.

A soluble antigenic extract of human blood lymphocytes from Example 1 or Example 2 was used to produce rabbit anti-human immunosuppressive antiserum. New Zealand white and Californian rabbits in the weight range of 2.2 kg. to 3.0 kg. were immunized according to the Lance schedule. One intramuscular (I.M.) injection of the antigen at 10 mg/ml., to which 100 units per ml. of streptomycin and polymyxin had been added, in Freund's Complete Adjuvant (F.C.A.) was given, and was followed by a course of four intravenous (I.V.) injections, in accordance with the schedule shown in Table 1.

TABLE 1

| Day | Injection Schedule Antigen | Bleed |
|---|---|---|
| 0 | I.M. 0.5 ml + 0.5 ml FCA | — |
| 14 | I.V. 0.5 ml | — |
| 21 | I.V. 0.25 ml | 10 ml |
| 28 | I.V. 0.25 ml | — |
| 35 | I.V. 0.5 ml | 10 ml |
| 46 | — | 15 – 20 ml |

At each bleeding, the removed blood from the animals was pooled, and allowed to clot. The serum was inactivated by heating at 56° C for 30 minutes, then allowed to cool. Fractionation was effected first by treatment twice with ammonium sulphate to remove most of the albumin, followed by absorption of the proteins other than the immunoglobulin Gon DEAE — Sephadex.

The A.L.G. so obtained had the following characteristics:

i. Molecular weight: 160,000 as determined by the method of Halsall (Ref. 1); during ultracentrifugation, a single component was observed sedimenting as a 7 S fraction.

ii. Toxicity:

a. Serial dilutions of the A.L.G. were titrated against the agglutination of human red blood cells (Ref. 10); at dilutions of protein up to one in twenty-four, the A.L.G. (originally 2% protein w/v) agglutinated human red blood cells.

b. Serial dilutions of the A.L.G. were titrated against the agglutination of human blood platelets (Ref. 11); at dilutions of protein up to 1 in 12 the A.L.G. (originally 2% protein w/v) agglutinated human blood platelets.

c. 1 ml samples, containing 60 mg. A.L.G. (dry weight), were injected intraperitoneally, into Swiss White mice. After 18 hours blood smears were prepared and the mice sacrificed. The blood smears showed a normal platelet count when examined microscopically, and no haemorrhages were detected after dissection and examination of the mice.

iii. Cytotoxicity: serial dilutions of the A.L.G. were tested for their ability to attack lymphocyte membranes, rendering them permeable to trypan blue, in the presence of guineapig complement (Ref. 12). At a dilution of 1 in 48 the A.L.G. solution (originally 2% protein w/v) rendered 50% of the lymphocytes in the test medium permeable.

iv. Rosette inhibition: serial dilutions of the A.L.G. were examined for their ability to inhibit the formation of rosettes of sheep red cells with human lymphocytes (Ref. 13). At a dilution of 1 in 32,000 the A.L.G. (originally 2% protein w/v) inhibited the rosette formation to the extent of 25%.

EXAMPLE 4:

Preparation of a soluble antigenic extract of human blood lymphocytes by hypotonic lysis Lymphocytes were isolated from fresh human blood by the method described in Example 1. The suspension of cells, containing $6 \times 10^9$ lymphocytes, was lysed by hypotonic treatment by the method of Example 1, and the solid cell debris was removed by centrifugation at 100,000 g for 30 minutes. The clear supernatant was collected and filtered through a Millipore GS membrane with a pore size of $0.22\mu$. The filtrate was dialysed against phosphate-buffered saline comprising an aqueous solution of a mixture of 0.85% w/v sodium chloride, 0.107% w/v anhydrous disodium hydrogen phosphate and 0.039% w/v sodium dihydrogen phosphate, at 4° C for 24 hours, and then concentrated by ultrafiltration using a Diaflo UM 10 [Amicon N.V. Mechelaarstraat 3 Oosterhout (N.B.) Holland] membrane which does not allow molecules with molecular weight greater than 10,000 to pass. The solid content of the extract, excluding salts as defined hereinbefore, consisted of 80% by weight of dry weight of extract of protein, with small amounts of lipid, carbohydrate, and nucleic acid. The ultraviolet absorption spectrum of the extract showed a broad absorption band around 240–320 m$\mu$, with a more intense absorption band around 210m$\mu$. The ratio of optical density at 280m$\mu$ to optical density at 260 m$\mu$ was 0.85. In the ultracentrifuge the extract showed a complex mixture, with most of the material having molecular weights between 50,000 and 150,000.

EXAMPLE 5:

Preparation of a soluble immunogenic extract of cultured lymphocytes, derived originally from human blood, by hypotonic lysis.

Lymphocytes were collected from human blood and purified as in Example 1. Cultures of these cells were established after stimulation with phytohaemagglutinin, using well-known procedures (Ref. 14). The established cultures were maintained in a medium containing 10% w/v foetal calf serum, and harvested when required. The cells were washed repeatedly in an aqueous solution of 0.85% w/v sodium chloride before being lysed.

Lymphocytes were lysed as described in Example 1 and the soluble extract was collected, dialysed, and ultrafiltered as described in Example 4.

The sample had a protein content of 75% by weight of the dry weight excluding salts, as hereinbefore defined. The ultraviolet spectrum showed an absorption maximum near 280 m$\mu$, typical of proteins, and indicating that the nucleotide content was low. In the analytical ultracentrifuge a distribution of molecular weights was observed, with most of the material at around 60,000 molecular weight (Ref. 1.). Electrophoresis on polyacrylamide gel (Ref. 2) indicated that the extract was a mixture of several proteins and was essentially similar to the extract described in Example 2.

EXAMPLE 6:

Preparation of non-toxic immunosuppressive anti-human blood lymphocyte sera using hypotonically-prepared extract.

A soluble extract of human blood lymphocytes prepared as described in Example 4, was injected into three rabbits as described in Example 3. Blood was collected 46 days after the start of the immunization procedure, clotted, and the sera thus obtained inactivated as described in Example 3. The sera did not cause internal haemorrhages when injected (1 ml. intraperitoneally) into mice, nor did they reduce the platelet content in the blood of the mice. The sera did not agglutinate human platelets. The sera gave titres in the lymphocyte agglutination, cytotoxicity, rosette inhibition, and haemagglutination tests as set out in Table 2. The tests were carried out as described in Example 3, using human cells, except that the titres represent dilutions of the whole, unfractionated sera.

| Rabbit | Lymphocyte Agglutination | Haemagglutination | Cytotoxicity | Rosette Inhibition |
|--------|--------------------------|-------------------|--------------|--------------------|
| 1 | 1/32 | 1/192 | 1/48 | 1/32000 |
| 2 | 1/32 | 1/24 | >1/2 | 1/16000 |
| 3 | 1/96 | 1/12 | >1/2 | 1/8000 |

The sera were also tested by immunofluorescence, to determine the highest dilution at which antibodies from the sera could be detected binding to human lymphocytes, the antibodies being detected using fluorescein-labelled goat-anti-rabbit$\gamma$-globulin. The sera 1, 2, 3 gave titres respectively of 1/32, 1/256 and 1/256 in this test.

EXAMPLE 7:

Preparation of non-toxic immunosuppressive anti-human blood lymphocyte sera using thiocyanate prepared extract.

A suspension of cells, containing $5 \times 10^9$ human blood lymphocytes obtained as described in Example 1, was centrifuged at 500 g for 10 minutes to sediment the cells. The supernatant was discarded and the cells were resuspended in an aqueous 2 M potassium thiocyanate solution at 4° C. The cells lysed immediately, giving a very viscous suspension. The suspension was diluted with an equal volume of an aqueous solution of 0.85% w/v sodium chloride whilst stirring vigorously in a Silverson homogeniser (Silverson Machines Ltd., London). The suspension was centrifuged at 100,000 g for 30 minutes and the supernatant was passed through a Millipore GS membrane with a pore size of $0.22\mu$, the entire procedure being carried out at 4° C. The thiocyanate was removed by extensive dialysis against an 0.85% w/v aqueous solution of sodium chloride. The extract was injected into two rabbits as described in Example 3. Blood was collected 46 days after the start of the immunization procedure, clotted, and the sera thus obtained were inactivated as described in Example 3. The sera showed similar properties to the sera described in Example 6, except that the sera did not agglutinate human erythrocytes, and the titres in all the immunological tests against lymphocytes were somewhat lower. The titres obtained in the various tests are set out in Table 3.

Table 3:

| Rabbit | Lymphocyte Agglutination | Haemagglutination | Cytotoxicity | Rosette Inhibition |
|---|---|---|---|---|
| 1 | 1/32 | >1/6 | >1/2 | >1/4000 |
| 2 | 1/8 | >1/6 | >1/2 | >1/4000 |

The sera were also tested by immunofluorescence as described in Example 6 and gave titres of 1/128 and 1/32 respectively.

EXAMPLE 8:

Pharmaceutical Preparation containing A.L.G.

A.L.G. produced in the manner of example 3 at a concentration of 7% w/v with 0.85% w/v sodium chloride in aqueous solution with, in addition, merthiolate at a concentration of 1/10,000 w/v, was sterilised by filtration through a Millipore GS membrane (pore size 0.22μ) and filled aseptically into ampoules each of which contained 100 mg. of A.L.G. protein (as determined by the biuret test), (Ref. 16). Samples of the filled material were tested for sterility, pyrogenicity, abnormal toxicity in laboratory animals, and by means of a number of standard tests for potency and non-specific reactions. This material was suitable for intravenous administration at a dosage of 20 mg. per Kg. body weight of patient.

References (Ref.)

Ref. 1:   Halsall; Nature; 215: 880, 1967
Ref. 2:   B. J. Davis; 1964 Ann. N.Y. Acad. Sci. 121: 404
Ref. 3:   E. Layne 'Methods in Enzymology' Vol. III: p. 454, Ed. Colowick & Kaplan, Academic Press.
Ref. 4:   O. H. Lowry et al; 1951, J. Biol. Chem. 193: 265.
Ref. 5:   Folch, Lees & Sloane Stanley; Fed. Proc., 13: 209, 1954.
Ref. 6:   Dreywood; Ind. Eng. Chem. (Anal. Ed.); 18: 499, 1946.
Ref. 7:   E. M. Lance et al; 1968, Immunology 15: 571
Ref. 8:   'Handbook of Experimental Immunology' Ed. D. M. Weir, Blackwell Scientific Publications Ltd., Oxford, 1967.
Ref. 9:   A. E. R. Thomson et al; 1966 Brit. J. Haematol. 12: 433
Ref. 10:  e.g. K. James et al; 1969 Immunochemistry 6:659
Ref. 11:
Ref. 12:  H. M. Abaza et al; 1966 Rev. Franc. Etud. Chem. Biol. 11:821
Ref. 13:  J. F. Bach et al; 1969 Transplantation 8: 265
Ref. 14:  'Cell & Tissue Culture' by J. Paul, 3rd Edition, E. & S. Livingston, Edinburgh & London, 1965.
Ref. 15:  Steinbuch and Audran; 1969 Arch. Biochem, Biophys. 134: 279
Ref. 16:  Leggett-Bailey; 1967 'Techniques in Protein Chemistry' Elsevier.

What we claim is:

1. A method of preparing an immunosuppressive and non-toxic antilymphocytic serum, comprising the immunisation of a mammal other than man with an immunogenically effective amount of a soluble immunogenic extract of human blood lymphocytes so as to immunise said mammal, removal of blood from said mammal, isolation of said serum from said blood, and the rendering of said serum sterile and isotonic;
   said extract comprising primarily a mixture of macromolecular components, each having a molecular weight between 10,000 and 1,000,000, a particle size not greater than 0.22 micron, a protein content of between 50 and 100%, a lipid content below 30% and a carbohydrate content below 20%, said percentage values being by weight of dry weight of said extract excluding salts, the solubility of said extract being such that 10 mg. of the extract in 1 ml. of 0.85% w/v aqueous sodium chloride solution is visually a clear solution.

2. A method of preparing an immunosuppressive, and non-toxic antilymphocytic immunoglobulin G, comprising fractionating an antilymphocytic serum as claimed in claim 1 to yield a therapeutically effective amount of an antilymphocytic immunoglobulin G, and rendering said immunoglobulin G sterile and isotonic.

3. A pharmaceutical composition comprising as an active ingredient an effective immunosuppressive amount of a sterile isotonic antilymphocytic serum and a stabiliser for said serum, said serum raised against an immunogenically effective amount of an aqueous, soluble, immunogenic extract of human blood lymphocytes in a mammal other than man, said extract comprising primarily a mixture of macromolecular components, each having a molecular weight between 10,000 and 1,000,000 a particle size not greater than 0.22 micron, a protein content of between 50 and 100%, a lipid content below 30% and a carbohydrate content below 20%, said percentage values being by weight of dry weight of said extract excluding salts, the solubility of said extract being such that 10 mg. of the extract in 1 ml. of 0.85% w/v aqueous sodium chloride solution is visually a clear solution.

4. A method of reducing the capacity of a mammal to respond to an immunogenic stimulus, comprising parenteral administration to said mammal of an effective immunosuppressive dose of a sterile, isotonic, solution of an immunosuppressive and non-toxic material selected from an antiserum and an immunoglobulin G fraction thereof, said antiserum having been raised in a mammal other than man against an immunogenically effective amount of a soluble extract of human blood lymphocytes, said extract comprising primarily a mixture of macromolecular components, each having a molecular weight between 10,000 and 1,000,000, a particle size not greater than 0.22 micron, a protein content of between 50 and 100%, a lipid content below 30% and a carbohydrate content below 20%, said percentage values being by weight of dry weight of said extract excluding salts, the solubility of said extract being such that 10 mg. of the extract in 1 ml. of 0.85% w/v aqueous sodium chloride solution is visually a clear solution.

5. An immunosuppressive, sterile, isotonic and non-toxic preparation comprising a therapeutically effective amount of an antilymphocytic serum raised against an immunogenically effective amount of an aqueous, soluble, immunogenic extract of human blood lymphocytes in a mammal other than man, said extract comprising primarily a mixture of macromolecular components, each having a molecular weight between 10,000 and 1,000,000, a particle size not greater than 0.22 micron, a protein content of between 50 and 100%, a lipid content below 30% and a carbohydrate content below 20%, said percentage values being by weight of dry weight of said extract excluding salts, the solubility of said extract being such that 10 mg. of the extract in 1 ml. of 0.85% w/v aqueous sodium chloride solution is visually a clear solution.

6. A preparation as claimed in claim 5 wherein the macromolecular components have a lipid content below 10% by weight of dry weight of the extract excluding salts.

7. An immunosuppressive, sterile, isotonic and nontoxic preparation comprising a therapeutically effective amount of an antilymphocytic immunoglobulin G isolated from an antilymphocytic serum raised against an immunogenically effective amount of a soluble immunogenic extract of human blood lymphocytes in a mammal other than man, said extract comprising primarily a mixture of macromolecular components, each having a molecular weight between 10,000 and 1,000,000, a particle size not greater than 0.22 micron, a protein content of between 50 and 100%, a lipid content below 30% and a carbohydrate content below 20%, said percentage values being by weight of dry weight of said extract excluding salts, the solubility of said extract being such that 10 mg. of the extract in 1 ml. of 0.85% w/v aqueous sodium chloride solution is visually a clear solution.

8. A preparation as claimed in claim 7 wherein the macromolecular components have a lipid content below 10% by weight of dry weight of the extract excluding salts.

9. A preparation as in claim 7 wherein said molecular weight is between 10,000 and 100,000.

10. A preparation as in claim 5 wherein said extract is prepared by lysing human blood lymphocytes to produce a lysate, separating a soluble portion having said solubility characteristic, and rendering said soluble portion sterile and isotonic with blood of said mammal.

11. A pharmaceutical composition as claimed in claim 3 wherein the active ingredient comprises an effective immunosuppressive amount of a sterile isotonic antilymphocytic immunoglobulin G fractionated from the serum defined in claim 10.

* * * * *

UNITED STATES PATENT AND TRADEMARK OFFICE
CERTIFICATE OF CORRECTION

PATENT NO. : 4,009,257

DATED : February 22, 1977

INVENTOR(S) : Derek Thomas et al

It is certified that error appears in the above-identified patent and that said Letters Patent are hereby corrected as shown below:

Column 1, line 1, "lumphocyte" should read --lymphocyte--

Column 3, line 7, "peferred" should read --preferred--

Column 4, line 51, "260µ" should read --260mµ--

Column 4, line 51, "280µ" should read --280mµ--

Column 4, line 58, "Lowery" should read --Lowry--

Column 5, line 8, "mannal" should read --mammal--

Column 5, line 10, "an" should read --than--

Column 5, line 57, "frm" should read --from--

Column 6, line 65, after "pH 7.4" delete "sodium"

Column 6, line 66, delete "chloride, 0.01 M.

Column 6, line 66, delete "[" and insert --sodium chloride, 0.01 M.--

UNITED STATES PATENT AND TRADEMARK OFFICE
CERTIFICATE OF CORRECTION

PATENT NO. : 4,009,257
DATED : February 22, 1977
INVENTOR(S) : Derek Thomas et al It is certified that error appears in the above-identified patent and that said Letters Patent are hereby corrected as shown below:

Column 7, line 26, "N-hydro-" should read -- $\underline{N}$-hydro- --

Column 7, line 60, "M" should read -- $\underline{M}$ --

Column 11, line 35, "121" should read -- $\underline{121}$ --

Column 11, line 39, "193" should read -- $\underline{193}$ --

Column 11, line 41, "13" should read -- $\underline{13}$ --

Column 11, line 43, "18" should read -- $\underline{18}$ --

Column 11, line 45, "15" should read -- $\underline{15}$ --

Column 11, line 52, "6:659" should read -- $\underline{6}$:659 --

Column 11, line 55, "11:821" should read -- $\underline{11}$:821 --

UNITED STATES PATENT AND TRADEMARK OFFICE
CERTIFICATE OF CORRECTION

PATENT NO. : 4,009,257
DATED : February 22, 1977
INVENTOR(S) : Derek Thomas et al It is certified that error appears in the above-identified patent and that said Letters Patent are hereby corrected as shown below:

Column 11, line 56, "8:265" should read --$\underline{8}$:265--

Column 11, line 60, "134" should read --$\underline{134}$--

Column 12, line 18, "claim 1" should read --claim 5--

Column 14, line 21, "claim 10" should read --claim 3--

Signed and Sealed this

Nineteenth Day of June 1979

[SEAL]

Attest:

RUTH C. MASON
Attesting Officer

DONALD W. BANNER
Commissioner of Patents and Trademarks